(12) United States Patent
Orban, III et al.

(10) Patent No.: US 10,327,837 B2
(45) Date of Patent: Jun. 25, 2019

(54) VESSEL SEALING INSTRUMENT WITH STEPPED JAW

(71) Applicant: Intuitive Surgical Operations, Inc., Sunnyvale, CA (US)

(72) Inventors: Joseph P. Orban, III, Norwalk, CT (US); Amy E. Kerdok, San Jose, CA (US); Hubert Stein, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 385 days.

(21) Appl. No.: 15/011,018

(22) Filed: Jan. 29, 2016

(65) Prior Publication Data

US 2016/0143688 A1  May 26, 2016

Related U.S. Application Data

(62) Division of application No. 12/164,388, filed on Jun. 30, 2008, now Pat. No. 9,265,567.

(51) Int. Cl.
| | |
|---|---|
| *A61B 18/14* | (2006.01) |
| *A61B 34/00* | (2016.01) |
| *A61B 34/37* | (2016.01) |
| *A61B 18/00* | (2006.01) |
| *A61B 34/30* | (2016.01) |

(52) U.S. Cl.
CPC .......... *A61B 18/1445* (2013.01); *A61B 34/37* (2016.02); *A61B 34/71* (2016.02); *A61B 34/30* (2016.02); *A61B 2018/0063* (2013.01); *A61B 2034/305* (2016.02)

(58) Field of Classification Search
CPC ............ A61B 18/1442; A61B 18/1445; A61B 18/1447; A61B 18/085; A61B 2018/145; A61B 2018/1452; A61B 2018/1455; A61B 2018/1457; A61B 2018/00607; A61B 2018/0063; A61B 34/71; A61B 2034/305
USPC ............................... 606/37, 50–52, 205–208
See application file for complete search history.

(56) References Cited

U.S. PATENT DOCUMENTS

| | | | |
|---|---|---|---|
| 1,918,889 A | 7/1933 | Bacon | |
| 3,367,337 A * | 2/1968 | Javna ..................... | A61B 17/12 24/489 |
| 3,608,554 A | 9/1971 | Mcguinness et al. | |

(Continued)

FOREIGN PATENT DOCUMENTS

EP    1301135 B1    9/2005

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Thomas A Giuliani
(74) *Attorney, Agent, or Firm* — Haynes and Boone LLP

(57) ABSTRACT

A vessel sealer has a stepped jaw that allows the jaw to have an overall shape and a width that provides desired strength, shape, and functionality while permitting a smaller raised portion to apply the sealing pressure. The smaller area applying the sealing pressure allows an actuating mechanism to apply a clinically desired sealing pressure without exceeding the force or torque limitations of the actuating mechanism and can limit thermal spread during a sealing procedure.

11 Claims, 3 Drawing Sheets

(56) References Cited

U.S. PATENT DOCUMENTS

| | | | |
|---|---|---|---|
| 6,206,903 B1 | 3/2001 | Ramans | |
| 7,329,257 B2 * | 2/2008 | Kanehira | A61B 17/3201 606/45 |
| 7,749,222 B2 | 7/2010 | Lu et al. | |
| 9,265,567 B2 | 2/2016 | Orban, III et al. | |
| 2003/0018331 A1 * | 1/2003 | Dycus | A61B 18/1485 606/48 |
| 2006/0020265 A1 | 1/2006 | Ryan et al. | |
| 2006/0271038 A1 * | 11/2006 | Johnson | A61B 17/07207 606/45 |
| 2007/0123855 A1 * | 5/2007 | Morley | A61B 18/1445 606/48 |

* cited by examiner

VESSEL SEALING INSTRUMENT WITH STEPPED JAW

CROSS-REFERENCE TO RELATED APPLICATIONS

This patent document is a divisional and claims benefit of the earlier filing date of U.S. patent application Ser. No. 12/164,388, filed Jun. 30, 2008, now U.S. Pat. No. 9,265,567, issue Feb. 23, 2016, which is hereby incorporated by reference in its entirety.

BACKGROUND

Minimally invasive medical procedures generally employ small diameter instruments that can be inserted through a small incision or a natural orifice to reach a work site inside the body of a patient. One type of instrument that is useful for minimally invasive procedures is a bipolar vessel sealer. A bipolar vessel sealer can seal a blood vessel by simultaneously clamping the vessel closed and directing an electrical current through the vessel tissue to cauterize the vessel tissue and thereby seal the vessel. Such vessel sealers generally have jaws that must be able to apply clamping pressure that is sufficient for sealing of the vessel. Another general requirement of a vessel sealer is that the jaws of the vessel sealer be long enough to hold a flattened vessel without the edges of the vessel protruding from the closed jaws. Accordingly, the jaws must be correspondingly longer for sealing larger vessels. Long jaws and high clamping pressures create reaction torques and forces in the structure of the vessel sealer. However, miniaturized instruments used in minimally invasive procedures generally have small components that are actuated using cables that extend along the length of a tube that is inserted in a patient. These components have strength limitations that limit the amount of force and torque that the vessel sealer can deliver.

The clamping pressure applied during vessel sealing is equal to the ratio of the applied force to the area over which the force is applied. Accordingly, the surface areas of the faces of the jaws of a vessel sealer can be reduced to achieve the desired clamping pressure without exceeding the force or torque limitations of the actuation structure. Since the length of the jaw is set by the size of the largest vessel to be sealed, only the width of the jaw can be decreased to reduce the area of the jaw face. However, there are limits in how thin jaws can be made. If the jaws of a vessel sealer are too thin, the jaws will be weak and could deflect or bend under load when sealing a vessel or when being used for purposes such as blunt dissection or grasping. Blunt dissection can use the tip of the vessel sealer to move or separate tissues and may apply forces that the thinnest portions of the jaws must support. Similarly, the vessel sealer could be used as a general grasper and would need the ability to securely grasp both fine and bulk tissue under varying loads. A vessel sealer is thus sought that can apply the clamping pressure required for reliable sealing of vessels without exceeding the strength limitations of the actuating structure while still being able to support working forces during use for vessel sealing or other purposes.

SUMMARY

In accordance with an aspect of the invention, a jaw of a vessel sealer includes a step having a raised or high portion that defines the area which applies sealing pressure to a vessel. The area of the raised portion can be made as thin as necessary to produce the desired sealing pressure without exceeding the force or torque limitations of the actuating mechanism. The thin area of the step does not make the jaw weak because a recessed or low portion can be sufficiently wide to keep the jaw strong enough to prevent bending during vessel sealing or other procedures (e.g., blunt dissection or grasping) performed using the vessel sealer. The step on the jaw additionally can be shaped to optimize the sealing function of the raised portion, to improve the grip or other clinical functionality of the raised or recessed portion of the jaw, or provide the jaw with a desired overall shape.

One specific embodiment of the invention is a vessel sealing instrument. The instrument can include a pair of jaws, an actuating mechanism, and an electrical system. At least one of the jaws has a face with a raised portion and a recessed portion. The actuating mechanism is coupled to bring the jaws together for a sealing procedure, and when tissue is between the jaws, bringing the jaws together causes the raised portion to apply pressure to the tissue. The electrical system can then be used to provide electrical signals to the jaws for sealing of the vessel.

Another embodiment of the invention is a medical procedure. The procedure includes applying a sealing pressure to a vessel by squeezing the vessel between a pair of jaws. At least one of the jaws has a face with a raised portion and a recessed portion, and the sealing pressure is only applied over an area of the raised portion. While the sealing pressure is applied, an electrical current can be run between the first jaw and the second jaw through the vessel to seal the vessel. The recessed portion can give the jaw the desired overall shape or strength, so that the method can optionally include performing other clinical functions such as blunt dissection using the jaws.

BRIEF DESCRIPTION OF THE DRAWINGS

Use of the same reference symbols in different figures indicates similar or identical items.

DETAILED DESCRIPTION

In accordance with an aspect of the current invention, the face of a jaw in a bipolar vessel sealer can be stepped. With a stepped jaw face, a raised portion of the jaw can contact and apply sealing pressure to a vessel, while a recessed portion of the jaw is away from the sealing surface. The overall width and profile of the jaw, which includes both the raised portion and the recessed portion, can thus be selected to provide a desired jaw strength, shape, and functionality, while the area over which sealing pressure is applied (e.g., the area of the raised portion) can be made sufficiently small to avoid exceeding the force or torque limits of the actuating structure and to minimize thermal spread. The stepped jaw thus permits accommodation of clinical goals that are conflicting for prior bipolar vessel sealers. In particular, the working length of jaw sealing surface and therefore the size of the vessel that can be sealed can be maximized without exceeding the force or torque limits of the actuating structure. At the same time, the overall width of the jaw may match the width and shape requirements for other uses of the vessel sealer. In particular, the outer shape and strength of the jaws is important when the instrument is used for procedures such as blunt dissection. Additionally, the overall width of the jaw can match the width employed in the actuating mechanism for the vessel sealer. In contrast, a narrow jaw, i.e., a jaw having an overall width selected for the maximum diameter of the vessels sealed, might need to transition to a greater width for assembly into isolation hubs at the pivot point of the jaw. This transition can take away from the sealing length of the jaw assuming the overall length from jaw tip to the pivot of the jaw is a fixed distance dictated by the limitations of the actuation mechanism.

Figure 1:
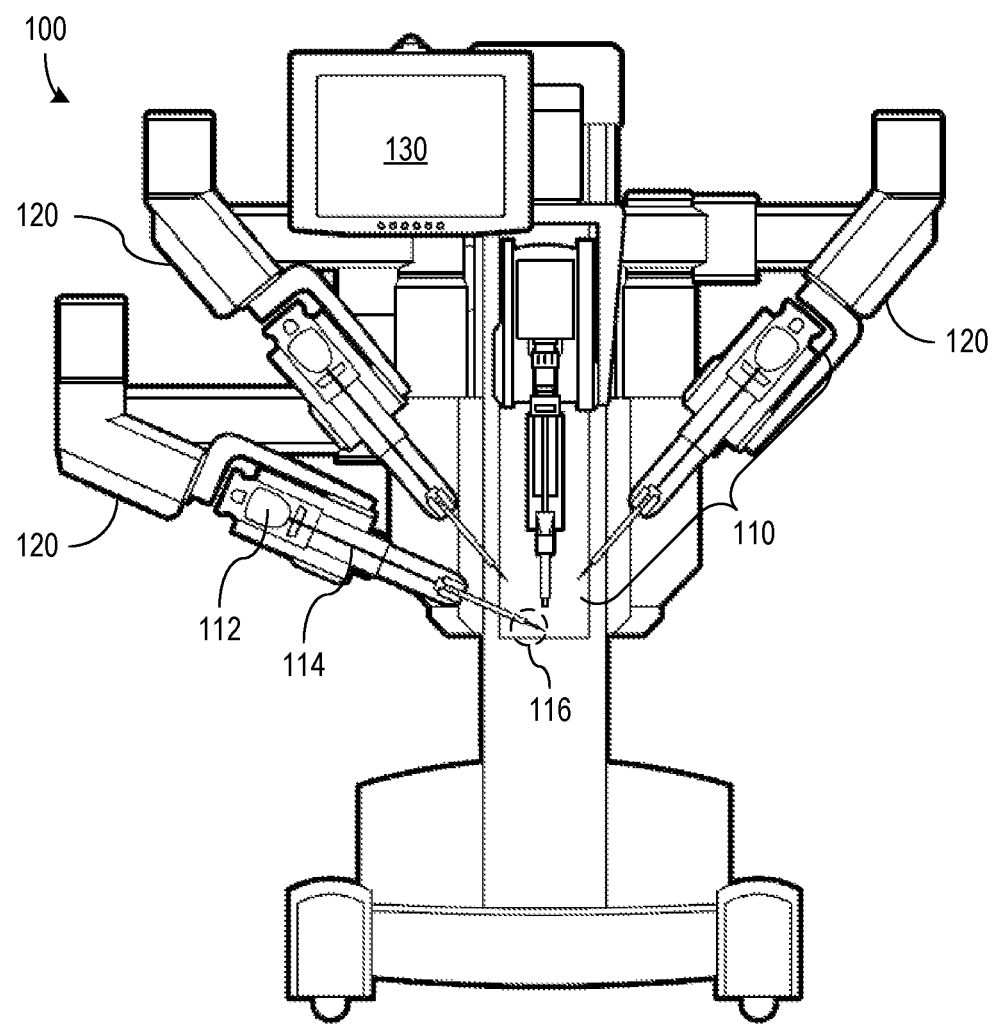
FIG. 1 shows a robotic system having multiple arms on which instruments for minimally invasive medical procedures can be attached.

Bipolar vessel sealing instruments in accordance with the invention may be employed in robotically controlled system capable of performing minimally invasive medical procedures. FIG. 1 shows an example of a robotically controlled system 100 capable of using a vessel sealing instrument in accordance with the present invention. System 100, which may, for example, be a da Vinci® Surgical System available from Intuitive Surgical, Inc. includes multiple medical instruments 110, each of which is mounted in a docking port on a robotic arm 120. The docking ports generally include drive motors that provide mechanical power for operation of instruments 110. The docking ports may additionally include an electrical system that provides electrical power for cautery or vessel sealing instruments and that optionally performs measurements such as measuring the impedance of tissue, for example, for determination of parameters of a sealing operation. Electrical systems for instruments 110 may alternatively be components separate from control system 100.

Each instrument 110 generally includes a transmission or backend mechanism 112, a main tube 114 extending from the backend mechanism 112, and an effector 116 at the distal end of the main tube 114. Drive cables and electrical conductors that are connected to effector 116 in an instrument 110 may extend through main tube 114 and connect to backend mechanism 112. Backend mechanism 112 typically provides a mechanical coupling of the drive cables to motorized axes provided by drive motors in control system 100. Control system 100 can thus control movement and tension in the drive cables as needed to position, orient, and operate effector 116. A processing system 130 of system 100 can provide a doctor or other operating room personnel with a user interface enabling manipulation of arms 120 to insert the ends of medical instruments 110 into small incisions in a patient undergoing a medical procedure and to operate effectors 116 once effectors 116 are at a worksite inside the patient.

Instruments 110 can be made interchangeable, so that the instruments 110 mounted on arms 120 can be selected for a particular medical procedure or changed during a medical procedure to provide the clinical functions needed. As is well known in the art, instruments 110 can implement many functions including but not limited to forceps or graspers, needle drivers, and scissors of many different shapes and sizes. In accordance with an aspect of the current invention, an instrument 110 can be a vessel sealer with a stepped jaw as described further below.

Figure 2A:
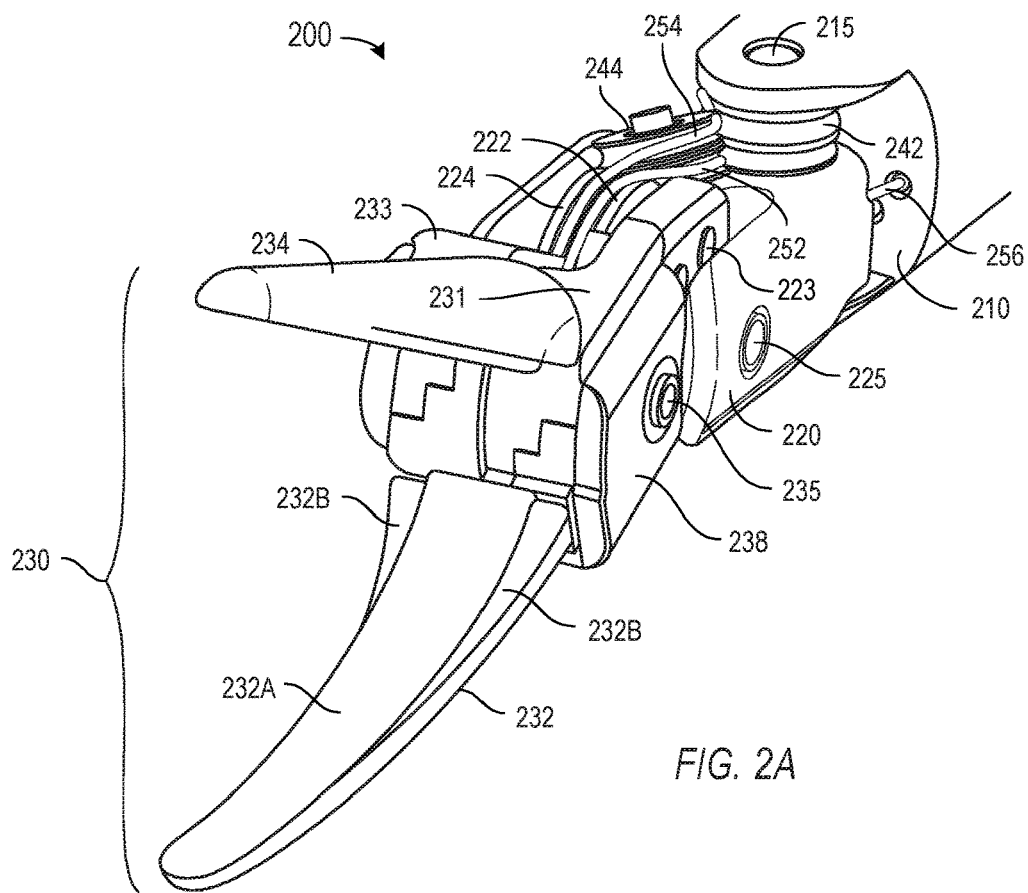
FIGS. 2A and 2B show different views of a wrist mechanism for a bipolar vessel sealer in accordance with an embodiment of the invention employing a step jaws.
Figure 2B:
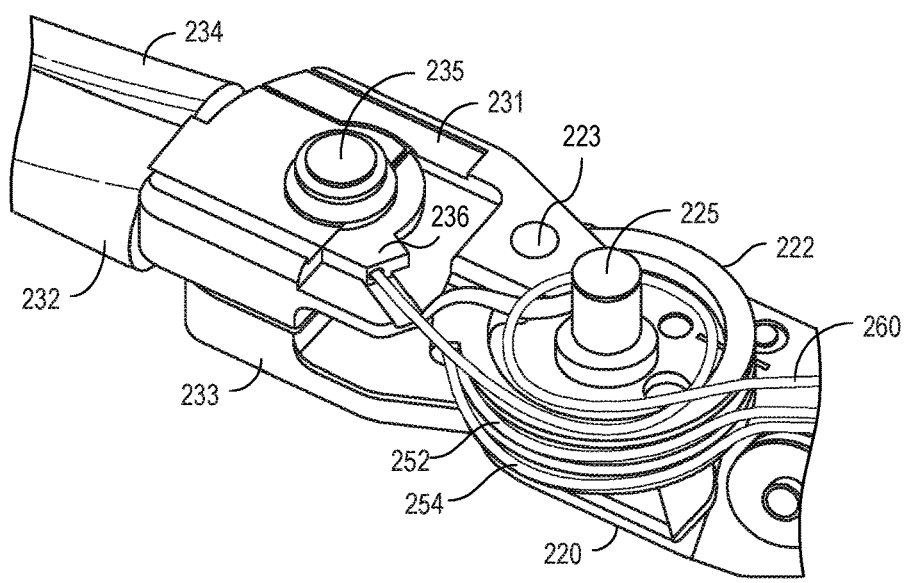

FIGS. 2A and 2B show portions of an actuating mechanism 200 for a bipolar vessel sealer that could be employed as an effector 116 of an instrument 110 in system 100 of FIG. 1. Mechanism 200 is described here merely as one example of an actuating mechanism capable of closing an effector to apply sealing pressure during a vessel sealing operation. Many mechanisms capable of implementing this function are known or could be developed and used with a stepped jaw in accordance with embodiments of the present invention as described further below. For example, U.S. Pat. No. 6,206,903, entitled "Surgical Tool with Mechanical Advantage," which is hereby incorporated by reference in its entirety, describes a wrist mechanism that provides a mechanical advantage to a grasper or forceps that could be electrified and employ stepped jaws in accordance with the present invention.

Mechanism 200 includes a proximal clevis 210 that attaches to the distal end of a main tube of an instrument, a distal clevis 220 rotatably mounted on proximal clevis 210, and an effector 230 mechanically coupled to the distal clevis 220. Mechanism 200 provides wrist movement to control the pitch, yaw, and grip of effector 230. For example, to control the pitch of effector 230, a pair of drive cables 256 (only one of which is visible in FIG. 2A) are connected to distal clevis 220, so that a backend mechanism (not shown) pulling on either cable 256 causes distal clevis 220 to rotate about a pin 215 in proximal clevis 210 and thereby changes the pitch of effector 230.

Effector 230 includes metal jaws 232 and 234 that are respectively attached to non-conductive extensions 231 and 233. Extensions 231 and 233 can be made of a high strength polymer such as polyetherimide (PEI) to be both insulating and capable of withstanding the torques applied to close effector 230. A non-conductive pin or hub 235 extends through jaws 232 and 234 and extensions 231 and 233, and forces applied to the ends of extensions 231 and 233 cause extensions 231 and 233 and jaws 232 and 234 to rotate about pin 235.

Mechanically coupled to the ends of extensions 231 and 233 are pulleys 222 and 224, respectively. For the mechanical coupling, each pulley 222 or 224 has an attached pin that fits into a matching hole in the corresponding extension 231 or 233. For example, a pin 233, which is visible in FIGS. 2A and 2B, on pulley 222 fits into a hole in extension 231. A similar pin on pulley 224 is not visible in the drawings. When pulley 222 or 224 rotates about a pin 225 of distal clevis 220, the pin on the rotating pulley 222 or 224 causes the attached extension 231 or 233 to rotate about pin 235. For rotation of pulley 222, drive cables 252, which may be the ends of a single cable loop, attach to pulley 222 and extend back around guide pulleys 244 and 242 and from there back through the main tube to the backend mechanism. When the backend mechanism pulls in a length of one of cables 252, pulley 222 rotates causing the end of extension 231 (and correspondingly jaw 232) to move. Similarly, when the backend mechanism pulls in a length of one of cables 254, pulley 224 rotates causing the end of extension 232 (and correspondingly jaw 234) to move. A backend mechanism coupled to cables 252 and 254 can thus cause jaws 232 and 234 to move independently or in a coordinated fashion to open or close effector 230 or change the yaw of effector 230. When closing, the maximum force that jaws 232 can apply without risking damage to mechanism 200 depends on the strengths and moment arms of components of mechanism 200 such as jaws 232 and 234, non-conductive extensions 231 and 233, and cables 252 and 254.

For a vessel sealing operation, pulleys 222 and 224 rotate to bring the ends of extensions 231 and 233 towards each other, causing jaws 232 and 234 to close and apply sealing pressure to a vessel caught between jaws 232 and 234. The contact face of jaw 232 includes a raised portion 232A and a recessed portion 232B. The lower elevation of recessed portion 232B keeps recessed portion 232B away from the tissue of the vessel being sealed, so that only the area of raised portion 232A applies the sealing pressure to the vessel. Accordingly, the force and torque applied to jaw 232 depends on the area of raised portion 232A, not the entire area of the face of jaw 232. Additionally, the area of raised portion 232A controls the amount of tissue heated during a sealing operation, and raised portion 232A can be selected to have a small area to minimize thermal spread and minimize the amount of tissue affected during the sealing operation.

Jaw 234 may have raised and recessed portions that respectively match portions 232A and 232B of jaw 232. However, a matched raised portion is not required, and in general, the sealing pressure will be applied in an area corresponding to the overlap of raised portion 232A with a raised portion of the face of jaw 234 or the entire face of jaw 234 if the face of jaw is flat.

In an exemplary embodiment, jaw 232 may be about 20 mm from pivot point 235 to the tip of jaw 232, while the sealing length of jaw 232 is between about 16 and 17 mm for sealing of vessels of up to about 10 mm in diameter. Raised portion 232A having an average width of about 3 mm would then provide a sealing area between about 48 to 51 mm$^2$. Recessed portion 232B can be recessed by about 0.3 to 0.5 mm relative to raised portion 232A if jaw 234 has a matching recessed portion or up to 1 mm or more if jaw 234 does not have a matching recessed portion. With such dimensions, clinically useful sealing pressures can be applied without exceeding the force and torque limitations of the structure of mechanism 200 even when the diameter of mechanism 200 is about 8 mm or less. The width of recessed portion 232B can be selected to provide the strength and jaw shape desired for other uses of effector 230. For example, in the embodiment illustrated in FIG. 2A, recessed portion 232B is on both sides of raised portion 232A, and starts with a width of about 1 mm for additional strength nearest pivot 234 of effector 230. The separate regions of recessed portion 232B then taper to a zero width to give jaw 232 the shape of a Maryland jaw.

An electrical current for the vessel sealing flows between jaws 232 and 234 through the tissue of the vessel trapped between jaws 232 and 234. The current will generally flow through the path of least resistance, which normally will correspond to the area of raised portion 232A. A pair of insulated wires or other electrical conductors 260 (only one of which is visible in FIG. 2B) makes electrical contact to respective jaws 232 and 234 in order to apply the electrical signals needed for sealing. In particular, wires 260 can be energized with opposite polarity AC electrical signals having a high voltage (e.g., about 600 volts) and a high frequency (e.g., a frequency greater than about 100 kHz). The resulting voltage difference across a clamped vessel causes a current that heats and seals the vessel.

The electrical signals that are activated for vessel sealing are isolated so that the AC current is only applied through jaws 232 and 234 and to thereby avoid causing unintended burns at other locations where the vessel sealing instrument contacts a patient or operating personnel. In mechanism 200, wires 260 have insulating coatings that prevent shorting to the main tube or the components of mechanism 200. Direct electrical contacts from wires 260 to metal jaws 232 and 234 are made by crimps. FIG. 2B shows where a crimp 236 attaches wire 260 to a conductive metal portion of jaw 232. Another crimp that is not visible in the figures can connect a wire carrying an opposite polarity electrical signal to jaw 234. As a result of the fixed connections of wires 260, rotation of jaw 232 or 234 causes the attached wire 260 to move. Each wire 260 has a service loop around pin 225 to provide slack or accept additional wire length as jaw 232 or 234 or other components of mechanism 200 move. Extensions 231 and 233 are made of non-conductive material, and electrically isolate jaws 232 and 234 from the remainder of mechanism 200. Non-conductive covers 238, one of which is shown in FIG. 2A but removed from FIG. 2B to better illustrate the electrical connections of wire 260, can be sealed on extensions 231 and 233, for example, using epoxy, to insulate the sides of jaws 232 and 234 and the contact structure of wires 260 and prevent current leakage.

Step jaws 232 and 234 can be varied in many ways in accordance with the different embodiments of the current invention. For example, jaws 232 and 234 have a curved shape but could have any other desired shape such as a straight or triangular shape. Further, raised portions 232A and recessed portions 232B are flat in the illustrated embodiment but may alternatively be curved or toothed provided that jaw 234 provides a surface that meshes with raised surface 232A. More generally, raised surface 232A and recessed surface 232B are raised or recesses relative to the corresponding face of jaw 234.

Figure 3A:
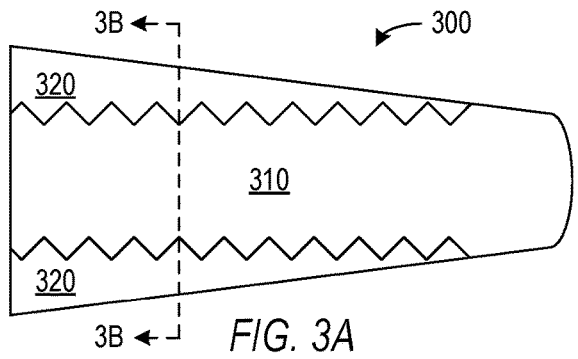
FIGS. 3A and 3B respectively show a plan view and a cross-sectional view of a stepped jaw with a raised portion that has a toothed edge in accordance with an embodiment of the invention.
Figure 3B:
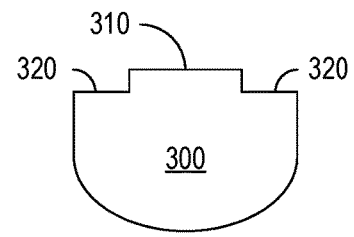

FIGS. 3A and 3B respectively illustrate a plan view and a cross-sectional view of a jaw 300 having a face with a raised portion 310 and a recessed portion 320. Raised portion 310 and recessed 320 together give jaw 300 a triangular shape overall. In the illustrated embodiment, raised portion 310 has a toothed edge, which can improve the gripping function of jaw 300 and avoid or reduce the problem of tissue sticking to jaw 300 after a sealing operation. More generally the shape of the raised area in a stepped jaw can be selected to have any shape that provides efficient vessel sealing, while the recessed portion is selected to give the jaw the desired overall shape, strength, or other functionality.

Figure 4A:
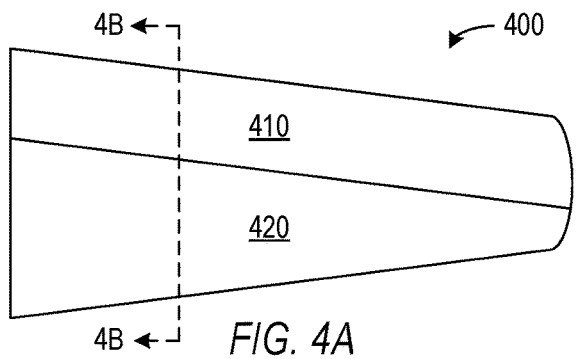
FIGS. 4A and 4B respectively show a plan view and a cross-sectional view of a stepped jaw in accordance with an embodiment of the invention having a raised portion along one edge of the jaw.
Figure 4B:
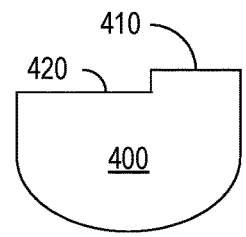

FIGS. 4A and 4B show a jaw 400 having a face with a raised portion 410 running along an edge of stepped jaw 400 and a recessed portion 420 running along an opposite edge of stepped jaw 400. With the illustrated configuration, a vessel sealer using jaw 400 has a sealing surface, e.g., raised portion 410, that may be easier to identify during a medical procedure because the edge of jaw 400 is easily identified visually even from back of jaw 400. In stepped jaw 400 and in other embodiments of the invention, the surface of the jaw opposite to the face of the jaw can be marked to visually identify the location of the sealing surface when the face of the jaw is not visible.

Figure 5A:
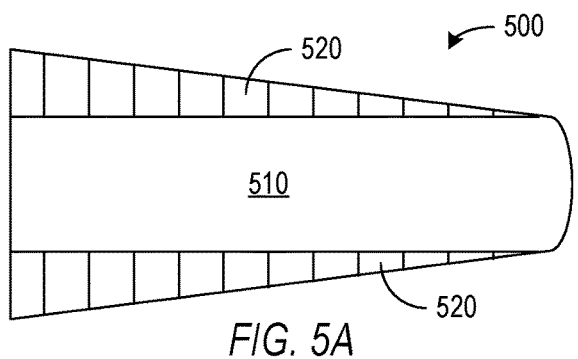
FIGS. 5A and 5B respectively show plan and side views of a stepped jaw in accordance with an embodiment of the invention having a recessed portion with teeth to improve gripping.
Figure 5B:
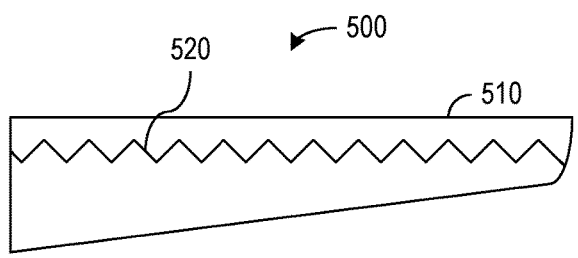

In accordance with a further aspect of the invention, the recessed portion of a stepped jaw can be shaped to perform clinical functions. FIGS. 5A and 5B show a stepped jaw 500 having a raised portion 510 and a recessed portion 520. Recessed portion 520 has teeth to improve the ability of jaw 500 to grip and hold tissue.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A vessel sealing instrument, comprising:
a first jaw including a metal portion having a first face with a raised portion and a recessed portion;
a second jaw including a metal portion having a second face;
an actuating mechanism coupled to the first and second jaws and operable to bring the first face and the second face together and to apply sealing pressure to tissue between the first and second jaw, wherein shapes of the first face and the second face limit the sealing pressure to an area of the raised portion; and
an electrical system coupled to drive an electrical current between the first jaw and the second jaw; wherein: a force limit of the actuating mechanism is greater than a force applied by the sealing pressure across the area of the raised portion; and simultaneously applying the sealing pressure across both the raised portion and the recessed portion of the first face would exceed the force limit of the actuating mechanism.

2. The instrument of claim 1, wherein the second face has a raised portion and a recessed portion, and the area to which the sealing pressure is limited corresponds to an overlap of the raised portion of the first face and the raised portion of the second face.

3. The instrument of claim 1, wherein the first jaw has a width that includes the raised portion and the recessed portion and that provides the first jaw with a strength to resist deflecting or bending, and wherein the area over which the sealing pressure is applied is narrower than the width of the first jaw to prevent the first jaw from deflecting or bending while the sealing pressure is applied.

4. The instrument of claim 1, wherein the actuating mechanism comprises a wrist mechanism and drive cables coupled to the wrist mechanism, wherein tension in one or more of the cables controls the sealing pressure.

5. The instrument of claim 4, further comprising a back-end mechanism that fits into a docking port of a control system and provides a mechanical coupling of the drive cables to motorized axes.

6. The instrument of claim 1, wherein the raised portion is in a central region of the first face and the recessed portion is on opposite sides of the raised portion.

7. The instrument of claim 1, wherein the raised portion is along a first edge of the first face and the recessed portion is along a second edge of the first face.

8. The instrument of claim 1, wherein the area of the raised portion has a toothed edge.

9. The instrument of claim 1, wherein the recessed portion has a toothed surface.

10. The instrument of claim 1, wherein the electrical system applies a first electrical signal to the first jaw and a second electrical signal to the second jaw, and the first and second electrical signals have opposite polarities.

11. The instrument of claim 1, wherein:
the first jaw and the second jaw are metal; and
the instrument further comprises a non-conductive pin or hub that extends through the first and second jaws.

* * * * *